(12) United States Patent
Mansmann

(10) Patent No.: US 9,066,802 B2
(45) Date of Patent: Jun. 30, 2015

(54) RIM ANCHORING SYSTEMS FOR FLEXIBLE SURGICAL IMPLANTS FOR REPLACING CARTILAGE

(71) Applicant: Formae, Inc., Paoli, PA (US)

(72) Inventor: Kevin A. Mansmann, Paoli, PA (US)

(73) Assignee: Formae, Inc., Paoli, PA (US)

( * ) Notice: Subject to any disclaimer, the term of this patent is extended or adjusted under 35 U.S.C. 154(b) by 0 days.

(21) Appl. No.: 14/208,327

(22) Filed: Mar. 13, 2014

(65) Prior Publication Data
US 2014/0207234 A1    Jul. 24, 2014

Related U.S. Application Data

(60) Division of application No. 13/452,980, filed on Apr. 23, 2012, now abandoned, which is a continuation-in-part of application No. 13/355,276, filed on Jan. 20, 2012, now Pat. No. 8,652,173.

(60) Provisional application No. 61/434,145, filed on Jan. 19, 2011.

(51) Int. Cl.
*A61F 2/08*    (2006.01)
*A61F 2/30*    (2006.01)
(Continued)

(52) U.S. Cl.
CPC .......... *A61F 2/30756* (2013.01); *A61F 2/3872* (2013.01); *A61F 2210/0019* (2013.01); *A61F 2/30767* (2013.01); *A61F 2/3094* (2013.01); *A61F 2/30965* (2013.01); *A61F 2/32* (2013.01); *A61F 2/389* (2013.01); *A61F 2/40* (2013.01); *A61F 2/4637* (2013.01); *A61F 2002/2821* (2013.01); *A61F 2002/30113* (2013.01); *A61F 2002/30115* (2013.01); *A61F 2002/30204* (2013.01); *A61F 2002/30225* (2013.01); *A61F 2002/30299* (2013.01); *A61F 2002/30354* (2013.01); *A61F 2002/30459* (2013.01); *A61F 2002/30461* (2013.01); *A61F 2002/30499* (2013.01); *A61F 2002/305* (2013.01); *A61F 2002/30604* (2013.01);
(Continued)

(58) Field of Classification Search
CPC .............. A61F 2/3872; A61F 2/30756; A61F 2002/305; A61F 2220/0025; A61F 2002/30495
USPC ...................................................... 623/14.12
See application file for complete search history.

(56) References Cited

U.S. PATENT DOCUMENTS 4,275,733 A    6/1981    Marinoff
5,944,759 A    8/1999    Link
(Continued)

FOREIGN PATENT DOCUMENTS

WO    0074554 A2    12/2000

OTHER PUBLICATIONS

European Search Report, EP 2617391A3, Jul. 31, 2013.

*Primary Examiner* — David H Willse
*Assistant Examiner* — Javier Blanco
(74) *Attorney, Agent, or Firm* — Duane Morris LLP

(57) ABSTRACT

Flexible cartilage-replacing implants are disclosed that use either or both of (1) enlarged peripheral rim components, and/or (2) elongated flexible reinforcing members that are embedded around the peripheral edge of an implant device. These types of anchoring devices, especially when used in combination, can provide flexible implants that can be implanted arthroscopically into synovial joints, for complete replacement of damaged cartilage segments.

5 Claims, 10 Drawing Sheets

(51) Int. Cl.
  *A61F 2/38*   (2006.01)
  *A61F 2/32*   (2006.01)
  *A61F 2/40*   (2006.01)
  *A61F 2/46*   (2006.01)
  *A61F 2/28*   (2006.01)

(52) U.S. Cl.
  CPC ............... *A61F 2002/30738* (2013.01); *A61F 2002/3085* (2013.01); *A61F 2002/30878* (2013.01); *A61F 2002/30892* (2013.01); *A61F 2002/4635* (2013.01); *A61F 2220/0025* (2013.01); *A61F 2220/0033* (2013.01); *A61F 2220/0066* (2013.01); *A61F 2220/0075* (2013.01); *A61F 2230/0006* (2013.01); *A61F 2230/0008* (2013.01); *A61F 2230/0065* (2013.01); *A61F 2230/0069* (2013.01); *A61F 2230/0093* (2013.01)

(56) References Cited

U.S. PATENT DOCUMENTS

| | | | |
|---|---|---|---|
| 6,328,758 B1 | 12/2001 | Tornier | |
| 6,371,958 B1 | 4/2002 | Overaker | |
| 6,520,980 B1 | 2/2003 | Foerster | |
| 6,530,956 B1* | 3/2003 | Mansmann | 623/18.11 |
| 6,540,770 B1 | 4/2003 | Tornier | |
| 6,585,730 B1 | 7/2003 | Foerster | |
| 7,144,415 B2 | 12/2006 | Del Rio | |
| 7,556,640 B2 | 7/2009 | Foerster | |
| 7,572,283 B1 | 8/2009 | Meridew | |
| 7,637,926 B2 | 12/2009 | Foerster | |
| 7,678,151 B2* | 3/2010 | Ek | 623/20.14 |
| 7,682,374 B2 | 3/2010 | Foerster et al. | |
| 7,695,494 B2 | 4/2010 | Foerster | |
| 8,157,805 B2 | 4/2012 | Re et al. | |
| 2002/0173855 A1 | 11/2002 | Mansmann | |
| 2003/0130695 A1 | 7/2003 | McDevitt | |
| 2004/0230315 A1* | 11/2004 | Ek | 623/23.51 |
| 2005/0202371 A1* | 9/2005 | McGuire | 433/201.1 |
| 2005/0287187 A1 | 12/2005 | Mansmann | |
| 2007/0224238 A1 | 9/2007 | Mansmann | |
| 2007/0288021 A1 | 12/2007 | Rickels et al. | |
| 2009/0132047 A1 | 5/2009 | Mansmann et al. | |
| 2010/0063542 A1 | 3/2010 | van der Burg | |
| 2010/0121348 A1 | 5/2010 | van der Burg | |
| 2011/0224801 A1 | 9/2011 | Mansmann | |
| 2012/0004725 A1 | 1/2012 | Shterling et al. | |

* cited by examiner

RIM ANCHORING SYSTEMS FOR FLEXIBLE SURGICAL IMPLANTS FOR REPLACING CARTILAGE

CROSS REFERENCE TO RELATED APPLICATION

This is a Division of application Ser. No. 13/452,980, filed Apr. 23, 2012, now abandoned, which is a Continuation-in-Part of application Ser. No. 13/355,276, filed Jan. 20, 2012, now U.S. Pat. No. 8,652,173, which claims the priority of provisional application 61/434,145, filed Jan. 19, 2011.

BACKGROUND OF THE INVENTION

This invention is in the field of surgical implants, and relates to devices and methods for repairing hyaline or meniscal cartilage in joints such as knees, hips, fingers, shoulders, etc.

In joints that are lubricated by synovial fluid, hyaline and meniscal cartilage segments provide smooth, slippery, lubricated (or lubricious) surfaces that enable bones to move and slide, relative to other bones. "Hyaline" cartilage refers to the types of cartilage segments that are affixed, in relatively thin layers, directly to bone surfaces (often called condyles). Background information on hyaline cartilage, and on surgical implants for replacing injured or diseased hyaline cartilage, is available from various sources, including several prior patent applications by the same inventor herein, such as Ser. Nos. 11/390,539 ("Implants for replacing hyaline cartilage, with hydrogel reinforced by three-dimensional fiber arrays"), 11/105,677 ("Hydrogel implants for replacing hyaline cartilage, with charged surfaces and improved anchoring"), and 10/071,930 ("Cartilage repair implant with soft bearing surface and flexible anchoring device").

Meniscal cartilage is more complex. Each knee joint has two meniscal segments, which are arc-shaped segments with triangular cross-sections, depicted in any textbook on anatomy. These meniscal segments are positioned on the left and right sides of each knee (referred to by physicians as the "medial" (inside) and "lateral" (outside) positions, and they help stabilize the femoral runners against "sideways" motion. Each meniscal wedge has two smooth and lubricious surfaces (a smooth lower surface, which is roughly horizontal, and a smooth upper surface, which is slanted and which curves sharply around the interior curved upper surface of the rounded wedge-type segment). These meniscal wedges are made of a specialized type of "fibrocartilage"; rather than being affixed, like a thin coating layer, on a bone surface they have anchoring ligaments, both at their tips (which attach to bone protrusions near the center of a tibial plateau), and around their peripheral surfaces (to the tendons and ligaments that form a "capsule" which encloses the knee and holds in the synovial fluid which lubricates the joint). Additional information on meniscal cartilage (as used herein, that term includes a structurally similar set of "labral" cartilage segments in hip and shoulder joints), and on the design of implants for replacing or repairing damaged meniscal or labral cartilage segments, is available from sources such as U.S. patent application Ser. No. 11/471,090, "Multi-part implants for combined repair of hyaline and meniscal cartilage in joints".

Joints that contain hyaline and/or meniscal cartilage (which includes labral cartilage) are referred to herein as "synovial" joints, since they are lubricated by synovial fluid. These joints can alternately be called "articulating" joints, because they involve joints having bone surfaces which move, relative to each other, in a manner referred to as "articulating" motion. The types of cartilage (and joints) of interest herein specifically exclude: (1) cartilage in spinal discs, which do not have any sliding surfaces, and which have a very different structure and bone-anchoring system, which actively prevents any sliding or shearing motions, since any such motion could severely injure the spinal cord; and, (2) other non-sliding, "non-articulating" cartilage, which is present in various body parts such as the nose, ears, windpipe, etc. Neither of those two types of cartilage (in spinal discs, or in ears, noses, windpipes, etc., not need to withstand the types of loadings and stresses that are imposed on synovial (i.e., articulating) joints. Therefore, implants which are designed to replace cartilage in spinal discs, or in ears, noses, windpipes, etc., do not require the types of specialized anchoring systems disclosed herein.

All implants of interest herein are specifically designed to be "substantially flexible", to a point which will enable "minimally invasive" surgical implantation, since flexibility can enable an implant device to be at least partially curled or rolled up, compressed, or otherwise flexed into a shape that can pass through a smaller incision than would be required by a non-flexible implant. Anything that can minimize the amount of cutting and disruption of soft tissues and vasculature, in and around a joint that is being repaired, will minimize damage to the surrounding tissues, thereby benefiting the patient and reducing pain, recovery times, risks of infection, etc.

The optimal type of minimally-invasive surgery on joints is arthroscopic surgery, in which all necessary instruments and devices enter a joint via small slits. In this type of surgery, any implant devices should be designed to allow passage through an arthroscopic insertion tube having the smallest practical diameter. Accordingly, the implants described herein preferably should be not merely slightly flexible; instead, an optimal implant should be flexible enough to be rolled up into a cylindrical configuration, to allow an implant to be inserted into a joint via an arthroscopic insertion tube.

If not adequately defined, the term "flexible" is inherently indefinite; for example, it can be argued that virtually anything that is not brittle or friable is (or can become) flexible, if enough force is applied. Therefore, a set of practical limits and "benchmark" standards is established and used herein, to define "flexible" (as that term is used in the claims), and to determine whether some particular implant has sufficient flexibility, on a practical level, to render it suited for use as disclosed herein.

Accordingly, a candidate implant device is deemed to be "flexible", as used in the claims, if the device (as manufactured and assembled in a form that will be removed from a sealed sterile envelope by a surgeon, immediately before implantation during a surgical procedure), meets either or both of the two following criteria:

(1) if it can be flexed (or curled, rolled, bent, etc.), without requiring tools, into a configuration that has an "angle of displacement" of at least about 70 degrees. By way of illustration, if one edge of the implant is held horizontal, on the surface of a table, the opposing edge must be capable of being lifted to an angle of at least 70 degrees from horizontal, which is equal to 20 degrees short of completely vertical.

(1) if it can be flexed, without requiring tools, into a configuration where its "width" (i.e., its smallest dimension, when looked at from a "top view" or "plan view") is reduced to about 80% or less of its width in a non-flexed, relaxed state. By way of illustration, if a femoral runner or a meniscal wedge can be temporarily "straightened out", from a curved and relatively semi-circular shape into a more linear shape that can be pushed into a joint via an insertion slit or tube, it can enable the insertion of the femoral or meniscal implant into a joint, with less damage to surrounding tissues.

If an implant as described herein is designed for replacing hyaline cartilage (which is relatively thin), it preferably should surpass those minimum levels of flexibility, and the implant should be capable of being rolled into a cylindrical configuration, for implantation via an arthroscopic insertion tube.

Shape-memory and Super-elastic Materials, and Nitinol

Since high levels of flexibility will be required for arthroscopic use of the implants disclosed herein, three specific terms of art in the field of materials science should be introduced and briefly explained. These three terms are shape-memory materials, super-elastic materials, and nitinol.

In general, "shape-memory materials" (SMM's, which includes various polymers as well as certain types of alloys) include any materials that fall within either of two somewhat different functional definitions.

Under the first definition, if a material can be deformed (such as by bending, stretching, etc.) in some way that appears to be stable, under some particular set of conditions, but if the material will return to its manufactured shape without suffering any permanent damage, when subjected to different conditions, then the material is classified as a "shape-memory material". A common parameter that is used to manipulate shape-memory materials, in ways that make convenient and valuable use of their "shape-memory" trait, is temperature.

For lack of a better descriptive term, the phrase "shape-memory materials" also acquired a second functional definition. If a certain alloy or polymer undergoes some type of "phase transition" which leads to a notably different type of physical performance or behavior, when subjected to a certain type of operating condition or parameter, and then it returns to its "normal" performance or behavior when returned to "normal" conditions, the term "shape-memory material" is often used as a label for that type of material, regardless of whether the different performance actually involves shape. This convention apparently arose when it was discovered, during the 1930's, that wires made of certain types of copper-zinc alloys would shrink, in length (which is indeed a change in shape), when heated; these types of wires came to be used in robotics and toys, as "muscle wires" that would contract, in length, when a current was applied to such wires in a way that caused heating of such wires.

A subsequent development that became of major medical importance arose when it was discovered, in the 1960's, that certain types of alloys containing nickel and titanium had an unusual behavior. Those alloys were called "nitinol" alloys (pronounced NIGHT-in-all), as a spliced acronym that combines the first letters from nickel, titanium, and "Naval Ordnance Laboratories", the federal research center where nitinol alloys were discovered. Nitinol alloys undergo a temperature-dependent transition that is the opposite of what occurs in most types of alloys and polymers. Most non-rigid alloys and polymers tend to become softer, and more flexible and pliable, when they are heated to higher temperatures. Nitinol alloys become of interest in medical devices, because they can do the exact opposite. At normal human body temperatures, nitinol alloys are in an "Austenite" crystalline form, which is relatively stiff. However, if a nitinol device is chilled in cold water (such as saline slush), it makes an entirely reversible transition to a "Martensite" crystalline form, which is substantially more flexible and pliable.

As a result of that unusual behavior, various types of medical devices are made of nitinol, such as stents (devices for holding blood vessels open, in people who suffer from partially blocked or occluded arteries such as in the heart or neck). These can be implanted and used as follows. If a stent, made of nitinol in the form of a cylindrical wire mesh, is chilled to a "Martensite" temperature (such as by immersing it in cold water), the stent can be compressed into a relatively small diameter that will fit inside a catheter tube, which can be "snaked" into a patient's body via a small incision, such as into a femoral artery. The stent can be kept chilled, while it remains in the catheter tube, by using cold water circulating through special channels in the catheter. After the stent reaches a blood vessel that needs to be unclogged, the catheter tube is withdrawn, allowing blood and surrounding tissues to warm the stent back up to its stiffer "Austenite" state. As that warming process occurs, the stent will expand back into its larger, unstressed, manufactured diameter, which will correspond to the inside diameter of the artery segment that needs to be kept open.

These types of nitinol devices, and the transitions they undergo at differing temperatures, are described and shown in more detail in numerous sources, including a website (www.nitinol.info) run by a company called Nitinol Devices and Components (NDC). Several short videos (about 1 minute each), which visually depict how nitinol alloys and devices behave, are available at www.nitinol.info\pages\technology.html. In addition, a review article by D. Stoeckel, "Nitinol Medical Devices and Implants", presented at the SMST 2000 Conference, is available at www.nitinol.info/pdf_files/stoeckel_1.pdf.

Accordingly, nitinol devices will not make self-directed transitions into shorter or longer lengths, or other different shapes, when chilled or heated. However, since they become more pliable and "workable" when chilled, they can be readily manipulated into useful shapes (for an implantation process or other purpose) at cold temperatures, and they will then return to a stiffer and stronger manufactured state and geometry, when allowed to warm up to body temperature. As a result, they are usually included within the class of materials called "shape-memory materials".

The term "super-elastic material" is broader, and it does not have a precise definition. As implied by the term "super", it includes materials with one or more elastic behaviors that would be regarded as super or superb (which implies especially useful, valuable, and somehow different and better), when compared to conventional elastic materials. In the field of metals, conventional elasticity can be represented and exemplified by long, thin, flexible pieces of stainless steel, or by the types of steel alloys used to make metal springs. In plastics and polymers, conventional elasticity is represented by latex rubber, silicon rubber, rubber bands, etc. Accordingly, "super-elastic materials" include materials that can substantially outperform those types of conventional materials, in one or more ways that involve elasticity. Since "shape-memory materials" that respond to temperature changes, and "muscle wires" that become either shorter or longer when electric currents are passed through them, both fall within that definition, those are often referred to as types of super-elastic materials.

One other point should be noted. In nearly all cases of interest herein, a device made from a shape-memory material usually will seek to return to a certain shape (which will be determined by the manufacturing process), when it returns to a "final" temperature (which will be body temperature, for any surgical implant) or other operating condition. This distinguishes shape-memory devices from items such as rubber bands. A rubber band is elastic, and it will return to a certain length, after any tension that caused it to take an elongated shape has been removed. However, a typical rubber band that has a substantial length will not attempt to return to a certain specific shape. If dropped onto a flat surface, it can come to rest in a relatively straight or oval-like configuration, or it can curve in either a right or left direction, without any substantial stresses arising within the rubber that makes the rubber band.

By contrast, in all cases of interest herein, a shape-memory device will have a predetermined shape, which must be created during a manufacturing operation (which can include various annealing, curing, treating, or other shape-imparting or shape-modifying steps). The device will then seek to return to that predetermined shape. This does not imply that the device must and will always return to exactly its manufactured shape; nevertheless, it will seek to do so, and any shape alterations that may be imposed on the device, by external mechanisms or forces (such as anchoring pins, an adhesive that is used to bond the material to another surface, etc.), will create some level of internal stresses within the shape-memory or super-elastic device.

Accordingly, proper design of a surgical implant made of a shape-memory or super-elastic material must take into account the final shape that the device will take, after it has been implanted in a particular location. Some implants are intended to impose mechanical forces on body parts or mechanical components that contact an implant; this is comparable to installing a spring-loaded device inside a mechanism. However, if creating that type of force is not the intent of a shape-memory or super-elastic implant device, then the implant should be manufactured with an unstressed shape that is as close as possible to the final shape the implant will take, after it has been implanted.

That is a brief introduction to a complex field of materials science. Much more information on these types of materials is available in books such as Otsuka and Wayman, editors, Shape Memory Materials (Cambridge Univ. Press, 1999), and from an organization called Shape Memory and Super-elastic Technologies (SMST), www.smst.org. A surgeon does not need to be an expert in this field of materials science, in order to be able to use and appreciate surgical devices that incorporate and use these types of materials. If a surgeon has a working knowledge of what these materials and devices can accomplish, and how they will perform when used in surgical implants, that is sufficient.

Returning to the subject of nitinol alloys, it was initially believed, by the Applicant herein, that certain types of rims or other anchoring components made of nitinol alloys would be ideal, for cartilage-replacing implants, because the use of nitinol alloys would allow them to become much more soft and flexible, by using a chilling process, during insertion into a joint that is being surgically repaired. However, additional research by the Applicant has identified an important obstacle to such use of nitinol alloys, in implants that will remain in a patient's body for an extended period of time. That obstacle involves a risk of corrosion, which is believed to arise primarily in areas where nickel atoms cluster together in "nickel-enriched" clusters or "pockets" that can have molecular structures and/or "lattice ratios" such as Ni3Ti. The bonds between adjacent nickel atoms are not as strong as the bonds between nickel and titanium atoms. As a result, during the manufacture of a nitinol component, if small pockets of material are formed that have nickel content greater than 50%, the nickel atoms in those pockets can be leached out, over a span of months or years, in ways that can lead to corrosion, cavities, and structural weakness.

It has been discovered, through testing, that a nitinol manufacturing process known as "Quick Cool with No Reheat" provides more corrosion-resistant nitinol alloys than a different process known as "Cool Down Slowly". Accordingly, nitinol alloys have been approved for use in some medical devices that are left in place for years, such as certain types of stents that help keep arteries open in patients who suffer from clogged arteries.

However, since the types of arthroscopically-insertable flexible implants being developed by the Applicant herein, for orthopedic use in load-bearing joints such as hips or knees (where any such implants will need to comply with stricter design requirements and constraints, compared to uses in non-load-bearing locations, such as stents) already have a number of novel and even pioneering features, when compared to conventional orthopedic implants that are in use today (as exemplified by conventional "total knee replacement" implants), this new and innovative "technology platform" is not well-suited for introducing new component and material selections that might trigger extensive additional long-term clinical testing requirements. Those types of long-term testing requirements could lead to severe problems and delays, especially if the main goal of such long-term clinical trials would be to ensure that a certain type of component material will not slowly corrode, over a span of a decade or more, in a mammalian joint.

Therefore, the Applicant herein began studying alternate types of candidate reinforcing devices, using materials that have long track records of biocompatibility with biological fluids and tissues, and which do not pose any risks or questions of potential slow and gradual corrosion. The results of those efforts are described below, as part of this invention.

However, it also should be noted that the use of nitinol, in cartilage-replacing implants designed for permanent implantation (in this context, phrases such as "long term" generally refer to time periods greater than at least 5 or 10 years, while "permanent" refers to the remaining life of a patient), might remain as a completely viable approach, if any such nitinol component will be completely embedded within a polymeric material that will effectively "seal in" (or entomb, or similar terms) the nitinol component, in a way that will prevent any nitinol from ever being contacted, in any significant quantities, by body fluids. That is indeed the design of various types of implants described and illustrated herein; accordingly, the use of nitinol anchoring rims, in such devices, remains as a potentially feasible, practical, and approvable design approach, in such implants.

Accordingly, one object of this invention is to disclose improved designs and constructions for flexible surgical implants that are designed and suited for arthroscopic repair and replacement of hyaline and/or meniscal cartilage, in synovial joints.

Another object of this invention is to disclose improved devices, assemblies, and methods for anchoring, to bone surfaces in synovial joints, flexible surgical implants which are designed for arthroscopic repair and replacement of hyaline cartilage.

Another object of this invention is to disclose improved devices, assemblies, and methods for anchoring flexible surgical implants designed for arthroscopic repair and replacement of damaged meniscal or labral cartilage.

These and other objects of the invention will be become more apparent through the following summary, drawings, and detailed description.

SUMMARY OF THE INVENTION

Improved designs are disclosed for flexible implants that will be used to surgically replace hyaline or meniscal cartilage, in synovial joints. In one preferred embodiment, a hydrophilic polymer, molded generally in the shape of a damaged cartilage segment that needs to be replaced, will have an enlarged peripheral rim that is substantially thicker than the interior portions of the implant. That enlarged peripheral rim will be designed to fit, in an accommodating manner, into a "groove" that will be machined (with the help of templates, computerized tools, etc.) into the bone surface that will receive and support the implant. This will create an interlocking-type "fit" that will provide greater strength and stability for the implant, to allow it to resist shear forces even during a fall, accident, or other moment of "peak loading" or peak stress.

If desired, a "stabilizing ring", which can be made of a shape-memory and/or super-elastic material (such as a "nitinol"-type alloy, if desired), or alternately from a braided or twisted multi-strand wire, cable, or similar component, can be embedded within the peripheral rim of the polymer component. This can allow the implant to be flexed into a cylindrical or other elongated, compressed, or other shape, for minimally-invasive insertion into a joint (such as via an arthroscopic insertion tube). After the implant has entered the joint, it will emerge from the insertion tube, or otherwise will be allowed or caused to return to its normal shape. This will enable the implant, with its enlarged outer rim containing a "stabilizing ring" component embedded within that rim, to perform a reinforcing and stabilizing role when the enlarged and reinforced flexible polymer rim of the implant settles into the bone groove.

The stabilizing ring also can be provided with means for securing the implant to anchoring components (such as bone screws) that can be emplaced before the implant is inserted into the joint. Alternately or additionally, the periphery of the implant can be provided with other anchoring means, either directly or indirectly, such as suture strands, cerclage wires, reinforcing mesh extensions, or other devices having "free ends" that can be secured to bone or soft tissue by various conventional means (including staples, sutures, screws, etc.), or by the types of racheting suture anchors which are described in more detail in related application Ser. No. 13/355,276 by the same Applicant herein.

BRIEF DESCRIPTION OF THE DRAWINGS

FIG. 6 illustrates only the anchoring system, and the central polymer component of the flexible implant is not shown. The enlarged rim of the flexible implant contains a reinforcing component having a non-flat cross-sectional shape, modeled after a metallic tape-measure that can be extended in stiffened form, and retracted into a compact roll. This shape can allow the reinforcing component to undergo a "collapsible transition" while it is being inserted into a joint; then, when the implant and rim return to their relaxed manufactured shape, the reinforcing component will again become stiffer and stronger.

DETAILED DESCRIPTION

Figure 1:
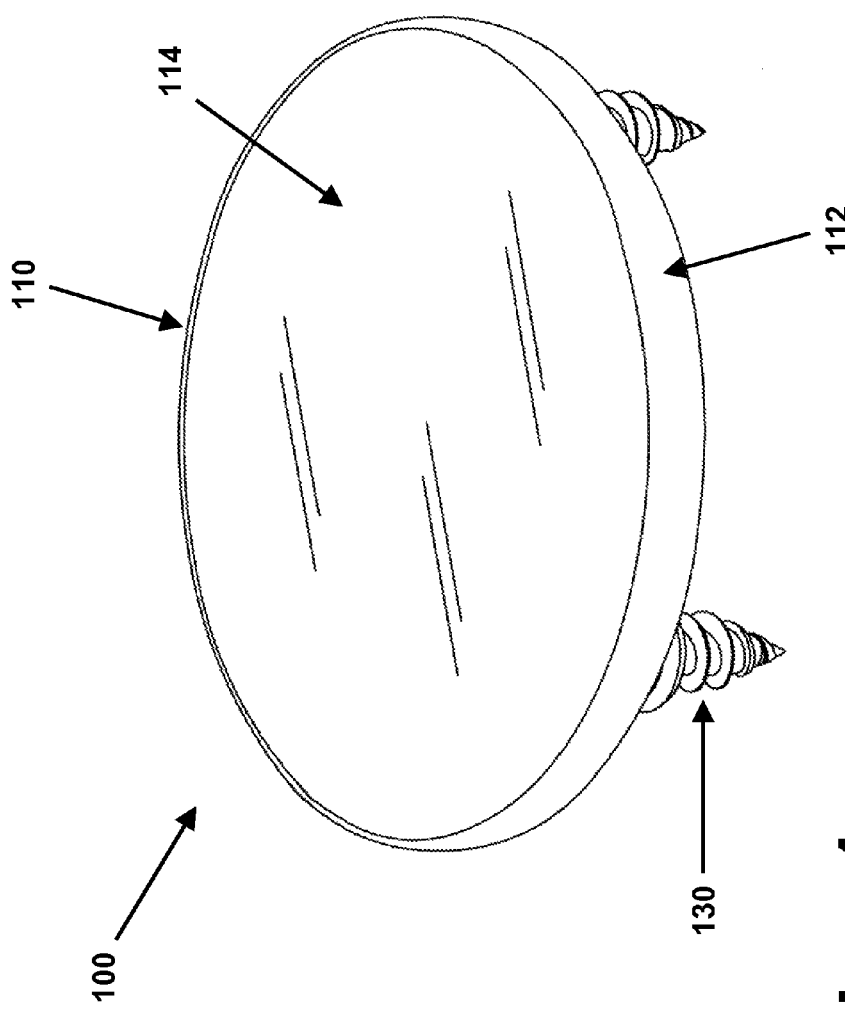
FIG. 1 is a perspective view of the upper (or exposed, or articulating) surface of a surgical implant for replacing hyaline cartilage, showing a flexible polymer component with a smooth and lubricious articulating surface, and also partially showing anchoring screws on the underside (or anchoring surface) of the implant.
Figure 2:
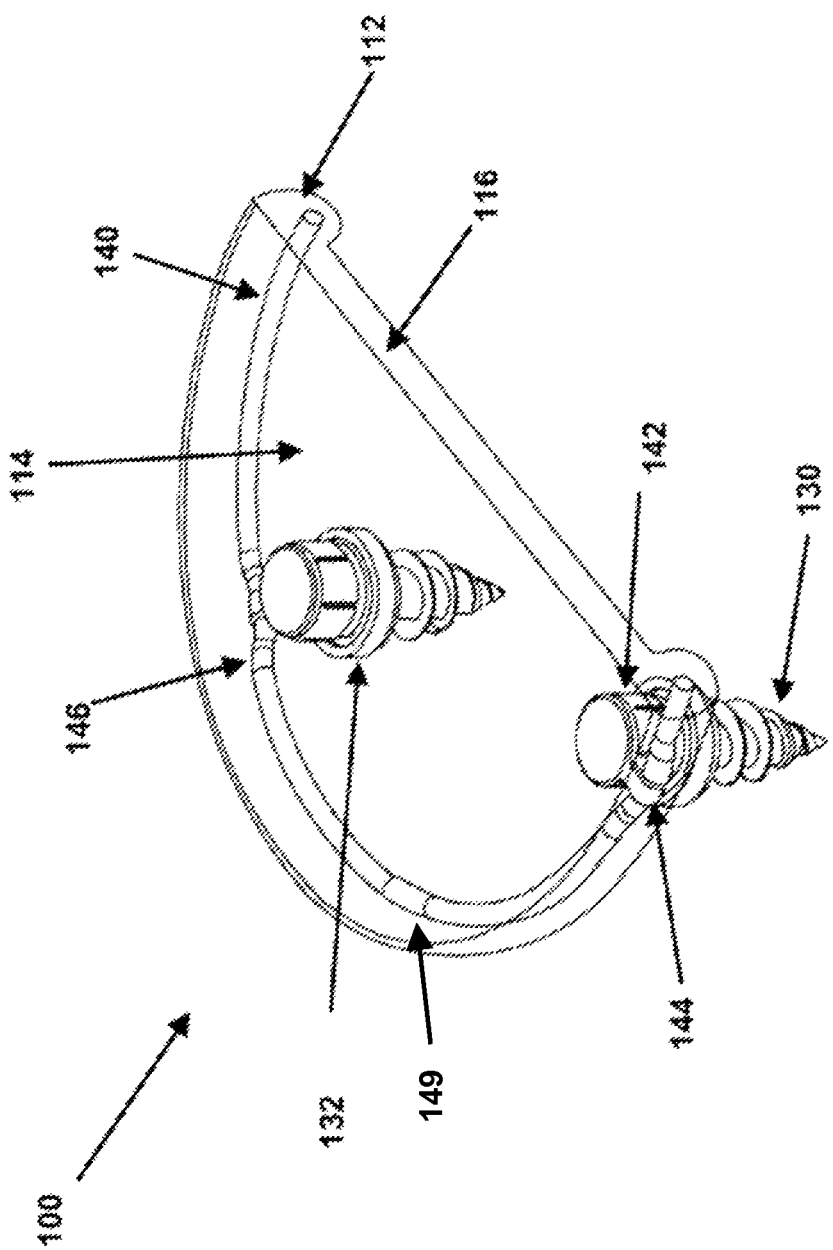
FIG. 2 is perspective cutaway view of the surgical implant, showing a flexible stabilizing ring (which can be made of a shape-memory or super-elastic material) that is embedded within an enlarged peripheral rim made of a flexible synthetic polymer. Screw-holder caps (which will snap onto the heads of anchoring screws, after the screws have been emplaced in a supporting bone surface) are affixed to the stabilizing ring, at spaced locations around the periphery of the implant.
Figure 3:
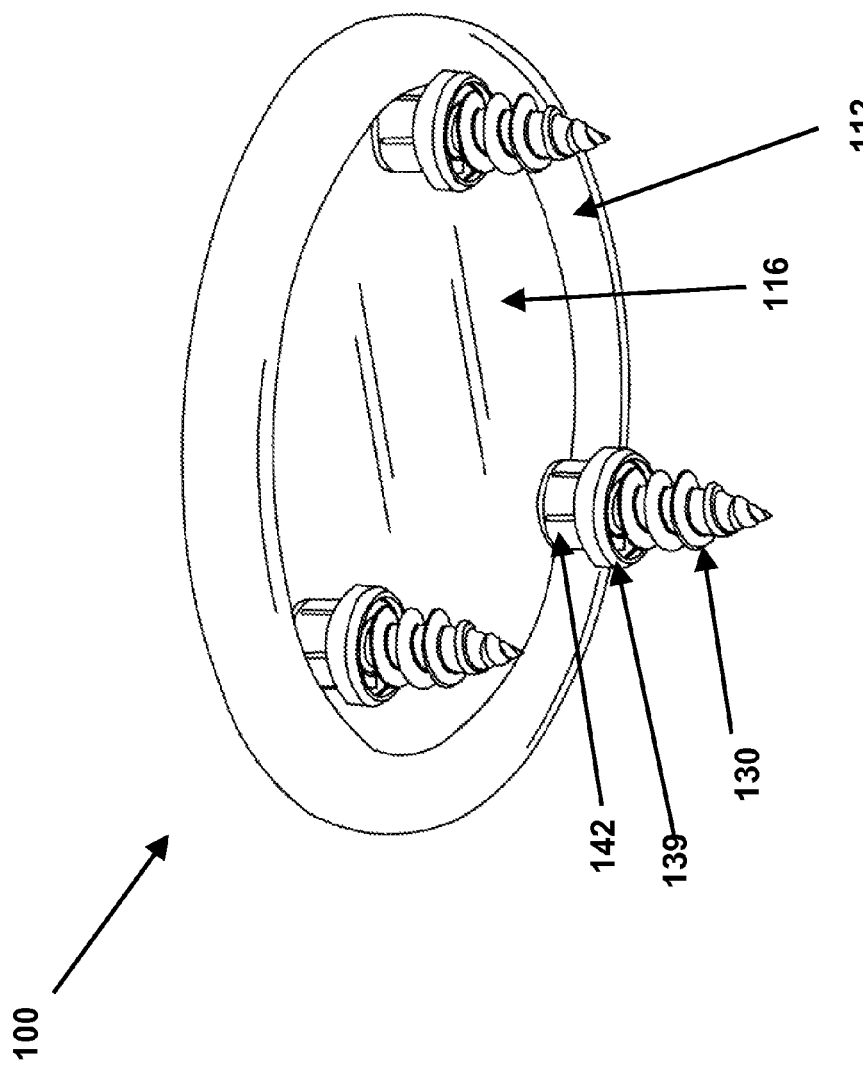
FIG. 3 is a perspective view of the anchoring surface (or underside, or similar terms) of the surgical implant shown in FIG. 2.

As briefly summarized above, a surgical implant 100, designed for replacing a relatively large segment of hyaline cartilage in a synovial joint such as a knee, shoulder, hip, etc.) is illustrated in FIGS. 1-3. Scaled-down implants with the same structures described herein, but with smaller diameters and thicknesses (and with only one or two anchoring screws, pins, or other components, which also can be smaller) also can be created for replacing hyaline cartilage in smaller joints, such as in thumbs, fingers, wrists, etc.

For simplicity of illustration, implant 100 is shown as having a generally round and flat shape. In actual use, any such implant designed for a large joint should have a molded and shaped articulating surface that will closely emulate the size and shape of the cartilage segment that is being replaced by the implant. The sizes and shapes of such cartilage surfaces (such as, within a knee joint, the medial and lateral femoral runners, the tibial plateau, and the patella (kneecap)), are all well-known to orthopedic surgeons. Such implants can be manufactured in an assortment of sizes and shapes, and a surgeon who is repairing a joint will select one or more implants having optimal sizes and shapes for a specific patient, based on X-rays or similar images or measurements of the joint that will need to be repaired.

On that subject, it should be noted that the irregular surface of a diseased, injured, or otherwise damaged or defective cartilage segment in any load-bearing joint typically will abrade and damage any other cartilage segment(s) that rub against the damaged and irregular surface; therefore, most such repairs will require at least two implant devices. For example, if a femoral runner needs to be replaced, then the portion of the tibial plateau which rubs and slides against the damaged femoral runner will likely also need to be replaced. This is conventional practice in this type of orthopedic surgery, and the implant devices described herein will be well-suited for such use, if manufactured in a range and assortment of sizes and shapes that will allow a surgeon to select suitably-sized implants based on the size, weight, and needs of any specific patient.

Returning to FIGS. 1-3, the polymer component 110 of an implant 100 preferably should be made of a single molded component to avoid and eliminate any surface seams (which can also be referred to as junctures, junctions, fissures, etc.) which otherwise might become potential weak spots, focal points for stress, and/or sites or sources of abrasion. Polymer component 110 comprises an enlarged peripheral rim 112 (shown in cross-section in FIG. 2), a smooth and lubricious articulating surface 114 (which will be coated and lubricated by natural synovial fluid, after implantation into a mammalian joint), and an underside or anchoring surface 116 (shown in FIG. 3). Any directional terms used herein (such as up, down, top, bottom, above, under, etc.) assume that a bone surface provides a horizontal "floor" (or base, support, foundation, etc.) for an implant, and the implant will rest on top of that horizontal base, with the anchoring surface (underside) of the implant resting upon the supporting bone surface, and with the articulating surface (which might can be called the "exposed" side of the implant) facing upward, on the "top" surface of the bone.

The types of polymers of interest herein can be manufactured by any of several molding methods that are known to those skilled in the art, using a flexible but tough and durable hydrophilic polymer, such as a suitable hydrophilic polyacrylonitrile (PAN) or polyurethane. As known to those skilled in polymer chemistry, terms such as polyacrylonitrile and polyurethane refer to the types of chemical linkages that are used to create the long "backbone" chains within such polymer molecules. Any of numerous types or combinations of "side groups" (also called moieties, pendant groups, and various other terms) and/or reactive crosslinking groups can be chemically bonded to the backbone chains. This is usually done by proper selection of the "monomer" reagents that are used to create a polymer; when monomer "links" are bonded to each other to form the long "backbone" chains in a polymer, the side groups that were present in the monomers will become pendant groups attached to the long backbone chains of the polymer. Accordingly, a polymer molecule which falls within a certain category or label (such as polyacrylonitrile, polyurethane, etc., as determined by the types of linkages in the long "backbone" chains) can be created with nearly any desired types of side (pendant) groups, which will impart a set of desired traits to the final polymer. It will be the side groups that will control whether a polyacrylonitrile, polyurethane, or similar polymer will be hydrophobic or hydrophilic, flexible or rigid, permeable or impermeable to water molecules, etc.

If desired, the exposed articulating surface of an implant of this type can be given a controllable negative electrical (ionic) charge, by means such as contacting the articulating surface for a controlled period of time with dilute sulfuric acid, as described in published U.S. patent application Ser. No. 11/105677, entitled, "Hydrogel implants for replacing hyaline cartilage, with charged surfaces and improved anchoring". This type of treatment can create a polymer surface that closely emulates the negative charge density of natural cartilage, which in turn will improve certain chemical interactions between the implant surface, and certain types of positively-charged components of synovial fluid.

The entire polymer component 110 (or any portion thereof) of an implant 100 can be reinforced by an embedded flexible fiber mesh, if desired, so long as the fiber mesh is not exposed on articulating surface 114, which must be kept extremely smooth and slippery. If desired, a portion of any such embedded mesh can extend outside of the peripheral rim 112, to provide additional anchoring means. Alternately or additionally, strands of anchoring material (such as suture strands, metal wires, flat polymeric or metal eyelets, etc.) and/or one or more sheets or segments of flexible mesh or drape material, also can be affixed to the implant (such as at or near the anchoring screws), either during the manufacturing process, or by a surgeon immediately before or during implantation, to provide additional anchoring strength and stability.

It should be noted that placing a "non-homogenous" member inside a polymer component can sometimes weaken the overall strength of the polymer component. Nevertheless, the types of reinforcing members disclosed herein can play highly valuable roles in achieving and providing truly stable and durable anchoring systems. Accordingly, any references to "reinforcing" components (or related phrases), as used herein, are used to refer to embedded or attached components that can lead to either or both of the following results or effects:

(i) a stronger component or assembly, such as a complete implant assembly having a molded polymer component that is able to withstand higher compressive, shearing, or other stresses and loads; and/or, (ii) a stronger, more secure, and more durable anchoring attachment to a hard bone surface or other tissue.

For simplicity of illustration, the "underside" (or "anchoring surface") 116 of implant 100 is depicted as a smooth surface, in FIG. 3. In an actual implant, the anchoring surface (which normally will contact and press against a prepared bone surface, from which damaged native cartilage has been removed) preferably should have a fibrous, porous, or similar texture that will actively encourage the ingrowth of scar and/or bone tissue, to provide stronger and more stable anchoring of the implant to a supporting bone surface (or other type of tissue, such as in the case of meniscal or labral implants). There are several known ways to create, in molded polymers, the type of porosity that will promote cellular ingrowth. Alternately, the underside 115 of polymer component 110 can be bonded to an additional layer of ingrowth-and-anchoring material, such as a screen or mesh layer made of several layers of very thin and flexible wires made of a titanium or other biocompatible alloy. In addition, any such anchoring surface can be coated or impregnated with one or more hormones or growth factors that will accelerate the ingrowth of tissue into the anchoring surface of the implant, to promote faster recovery after the surgery.

In a preferred embodiment, a stabilizing ring 140 is embedded within the flexible polymeric component of peripheral rim 112. Ring 140 can also be referred to by various other terms, such as an anchoring component or anchoring ring, or as a cable ring, cable anchor, anchor cable, or similar terms if it is made of a cable-type material. The term "cable" as used herein implies an elongated flexible component made from a multi-stranded material, which in most cases will be a flexible metal, or a synthetic polymeric material, such as "ultra-high molecular weight polyethylene" (UHMWPE).

If desired, ring 140 can be made of a "shape-memory" or "super-elastic" material. Because a component which is fully embedded within a polymer component will not be contacted by body fluids in any appreciable quantity, a "nitinol"-type alloy can be used for this type of embedded component, if desired, despite the risks of gradual corrosion that can occur over a span of years or decades when nitinol alloys are contacted by body fluids. Alternately, to alleviate potential regulatory concerns, and to render safety- and durability-testing easier, a shape-memory, super-elastic, or other polymer can be used to make stabilizing ring 140; or, stabilizing ring 140 can alternately be made of a twisted or braided multi-strand cable, as described below and illustrated in FIGS. 7 and 8.

The type of implant assembly shown in FIGS. 1-8, containing a flexible stabilizing ring 140 embedded within an enlarged flexible polymeric component around the peripheral outer rim 112 of an implant device, can allow a flexible surgical implant of this type to be bent, rolled, or otherwise flexed (without requiring tools, and with tolerable stresses that will not cause any lasting damage to the implant) into a cylindrical or compressed shape, for insertion into a joint via an arthroscopic insertion tube.

If the shape-memory and/or super-elastic stabilizing ring has a temperature-dependent behavior that causes it to become more flexible and less rigid when it is chilled, then it can be chilled, immediately before flexion and insertion, by a suitable step such as immersing it in a bowl of ice-cold saline slush. As the implant warms back up to body temperature, after it is inside the joint, the shape-memory stabilizing ring will stiffen, imparting a reinforced final shape to the implant.

Alternately, if the stabilizing ring is made of a super-elastic material that does not require temperature manipulation to give it high levels of flexibility, then no such treatments are required, and other approaches can be considered. For example, if an elongated component made of a super-elastic material has a half-circle or arc-shaped cross-section, similar to the cross-sectional shape of a tape measure, as depicted in the stabilizing ring shown in FIG. 6, then it can offer substantial resistance to bending, but only up to a certain point (or level, extent, or similar terms) of flexion. When that point or level is reached, the arc-shaped cross-section will be forced and flattened into a linear cross-section, in a manner comparable to what happens to a metallic tape measure when it is retracted into a carrying case. After that type of flattening transitional deformation occurs, at one or more locations around the rim of an implant that is being flexed and rolled up, the stabilizing ring component can be bent with almost no resistance, thereby allowing an implant with this type of stabilizing ring to be inserted into a joint via an arthroscopic insertion tube. Once the implant is inside the joint, it is allowed to relax and return to its manufactured size. When that occurs, the stabilizing ring will regain its original cross-sectional arc shape, and when that occurs, it will become much stiffer, in a way that will render it ideally suited for reinforcing, stiffening, and strengthening a cartilage-replacing implant.

Regardless of which specific approach is used, a stabilizing ring made of a shape-memory or super-elastic material can perform its reinforcing role, once the rim of an implant with that type of embedded ring has been properly positioned in a groove that has been machined (by the surgeon, with the help of templates, computerized tool guides, etc.) into the bone surface that will support the implant.

In a preferred embodiment, stabilizing ring 140 can be provided with means for securing the implant to anchoring components, such as bone screws. Alternately or additionally, the periphery of the implant can be provided with other anchoring means, either directly or indirectly, which can be secured to bone or soft tissue by various known means, including staples, sutures, screws, etc.

Figure 4:
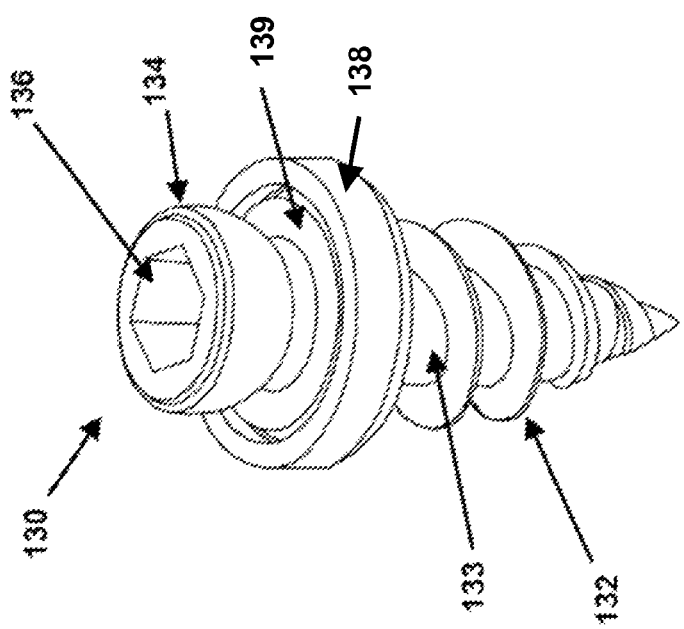
FIG. 4 is a perspective view of an anchoring screw, with a rounded "snap cap" head, and with a "shoulder ring" affixed to the neck of the screw, which will press against a stabilizing washer that will press against a bone surface.

In the embodiment illustrated in the drawings, three anchoring screws 130 will be emplaced in the supporting bone, before the implant is inserted into the joint. This can be done with the aid of pilot holes that will be drilled into a prepared bone surface (from which the native cartilage has been removed), using a template or computerized guiding tool to establish the proper locations and angles of the screw holes and screws. As shown in FIG. 4, the threads 132 of each bone screw 130 (on shaft 133) will have sizing and spacing suited for bone anchoring, and each screw head 134 will have a rounded outer shape, to allow a "snap cap" 142 (affixed to stabilizing ring 140) to be secured to a screw, by simply pressing snap cap 142 onto a screw head 134. Torsional driving means (such as a hex socket 136, as shown in FIG. 4) should be provided on each screw head 134, to enable the surgeon to drive each screw 130 into the bone, to a desired depth.

If desired, an enlarged "shoulder ring" 138 (or washer, or similar terms) can be provided around the "neck" of each bone screw 130. The shoulder ring 138 can press directly against the bone surface if desired; alternately, it can settle into an accommodating washer component 139. If a washer component 139 is used, the bottom surface of shoulder ring 138 preferably should have a beveled, angled, or rounded surface, rather than a completely flat and planar disc-type rim, and the "seating surface" inside washer component 139 should have an accommodating beveled or rounded surface. This will enable more stable and secure seating of the screw 130 in washer component 139, if a slight misalignment occurs where a screw hole drilled into a bone surface is not exactly perpendicular to the bone surface at that location.

Figure 5:
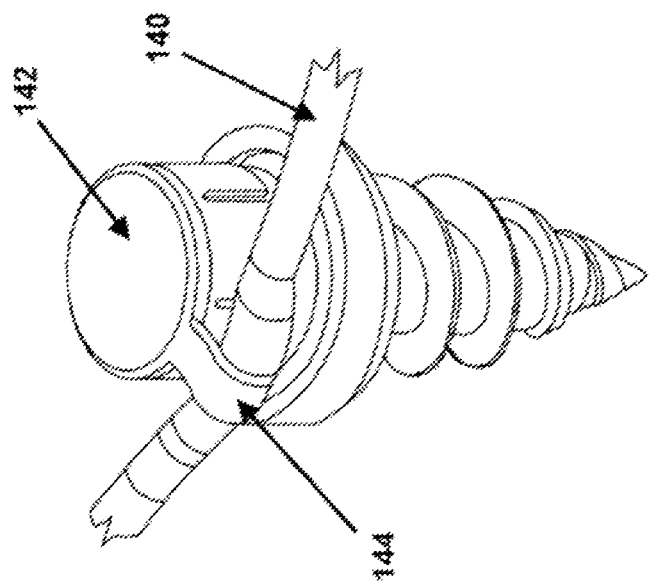
FIG. 5 is a perspective view of screw-holder cap, affixed to a stabilizing ring of an implant, which has been pressed and "snapped" onto the rounded head of an anchoring screw.

As shown in greater detail in FIG. 5, each "snap cap" 142 can be secured to stabilizing ring 140, by any suitable means, such as a protruding tab (or finger, strap, or similar terms) that can be bent into a loop structure 144 that will encircle ring 140. At each of the spaced attachment locations around the length of stabilizing ring 140, a "coupling detente" 146 can be provided. In this context, this type of "coupling detent" can refer to a localized bend, a drilled hole, a welded or crimped component, or any other device or component that will prevent sliding, slippage, or other displacement of the loop structures 144 (or similar components) along the length of an anchoring rim 140, when those components are embedded within a polymer component.

In one preferred embodiment, coupling detentes 146 can consist of a "bend" that places the actual coupling location (i.e., the site where loop 144, on a "snap cap" 142, wraps around anchoring rim 140) closer to the surface of the bone that will support the implant. Coupling detentes that have this arrangement can provide anchoring components that are partially or fully "countersunk", in a manner that allows the top of a screw head, "snap cap", or other anchoring structure to be "lower" (i.e., closer to and possibly aligned or "flush" with the bone surface), with less protrusion. This arrangement can reduce the risk that a protrusion (or bump, hump, etc.) at the site of an anchoring component might either (i) damage the flexible polymer component of an implant, or (ii) create an unwanted irregularity in an otherwise flat or smoothly-rounded articulating surface, after an implant has been installed.

If desired, stabilizing ring 140 can be provided with a closure sleeve 149 (illustrated in FIG. 2), to hold the two ends of a stabilizing ring 140 together. If used, this type of closure sleeve 149 can be secured to the two ends of a strand, cable, or other components, by means such as crimping, a rivet, "snap rings" inside the sleeve 149, or similar means. In general, shape-memory and super-elastic materials are not well-suited for welding, and the types of stresses imposed on them often focus on any junctures or interfaces, in ways that often render glue or epoxy unreliable, and prone to failure. Therefore, other means of securing the two ends of a stabilizing ring, to each other, must be used, such as a crimped closure sleeve that tightly grips both ends of a ring.

Another configuration that merits evaluation would use a "key-ring" arrangement, in which the two ends of the stabilizing ring 140 overlap each other, for some distance. Since both of the two ends will be embedded within a tough and durable polymer (if desired, a metallic or other sleeve can be tightly wrapped and/or crimped around at least a portion of any such overlap), this approach is likely to be useful in at least some designs, especially non-circular designs. Any such juncture preferably should be positioned, within any stabilizing ring in an implant as disclosed herein, in a location that will not be subjected to high flexure-related stresses, during the insertion stage of the operation. For example, if a femoral runner implant has a shape comparable to a ellipse or an oval-type racetrack, the juncture location preferably should be positioned near the middle of the most nearly straight portion of the ring, rather than near the "apex" of a curved portion of the ring.

Alternately, it is feasible and practical to provide a gap between the two ends of a stabilizer ring, if desired. Since the nature and purpose of the ring is simply to provide stabilization for the implant after the enlarged peripheral rim of an implant has settled into an accommodating groove or trench that has been machined into the surface of the supporting bone, there is no specific need for the stabilizer ring to extend around the entire peripheral rim of an implant. For example, each femoral runner implant can be provided with an enlarged peripheral rim made of molded polymer material, which will contain embedded stabilizer segments mainly located around the "curved ends" of the implant, while the two "side" portions (medial and lateral) of the implant periphery might contain stabilizer segments that are long enough to provide secure anchoring attachments at or near all of the ends of the segments, but which do not comprise a complete "ring" that fully encircles and surrounds the implant.

The molding and fabrication methods that will be required to make these types of implants are well within the level of ordinary skill in that field of art. Any of various mechanical means can be used to suspend a stabilizing ring at an appropriate height and position in a mold cavity, while a liquid "pre-polymer" is poured into the mold cavity, so that the stabilizing ring will be properly centered and embedded within the enlarged peripheral rim of the implant after the "pre-polymer" mixture has set (or cured, hardened, polymerized, etc.) to form the flexible polymer. For example, if the stabilizing ring of an implant has "snap caps" affixed to it, which are designed to be snapped onto the rounded heads of anchoring screws that have been emplaced in a supporting bone, then the molding cavity can include (or interact with) a device (often called a "jig") that will have the same number of rounded screw heads, positioned in the same spatial relationship with respect to the enlarged rim vacancy in the molding cavity.

Optimal designs for different types and sizes of implants, for different types of joints and among different classes of patients, are likely to vary substantially. For example, finger and thumb joints are small, and do not need to withstand nearly the loadings and stresses that are imposed on knee joints; accordingly, implants as disclosed herein for repairing finger or thumb joints can rely entirely on suture strands that are wrapped around a peripheral anchoring cable, and that emerge from the outer rim of the molded polymer component. By contrast, in most patients, implants for repairing a femoral runner or tibial implant, in a knee joint, will need to withstand much greater loads and stresses. Accordingly, any implants used for knee repairs normally should utilize a combination of bone screws and suture strands; however, even that presumption will need to be assessed, for each individual patient, by a skilled orthopedic surgeon, depending on the status and needs of the patient. For example, if a surgeon is treating an elderly woman who is suffering from serious osteoporosis and/or brittle bones, the surgeon might decide that bone screws would pose an unacceptable risk of damaging that patient's already-fragile bones, so other anchoring means should be used instead of bone screws.

Accordingly, when such factors are taken into account, the design options that should be considered, for specific types and classes of implants, become somewhat broader, and the following factors should be taken into account.

For implants that will remain under relatively steady or low-level compressive loadings that do not need to withstand high shear stresses, such as in finger or thumb joints, relatively aggressive anchoring components such as screws may not be required. Devices such as staples, sutures, and/or pins made of swellable materials (or using "spring-type" gripping mechanisms) can provide adequate alternatives for at least some such implants.

In addition, depending on the depth and shape of a groove or trench that will be machined into a bone surface to provide an accommodating "seating component" for the enlarged rim portion of an implant as disclosed herein, it may be preferable in some cases to eliminate additional anchoring components, and rely on a combination of other anchoring meands, such as: (1) bone cement; (2) one or more suture strands that are firmly secured to a flexible anchoring cable that is embedded within the polymeric rim of an implant; and/or, (3) "seating" of the enlarged rim component, within an accommodating groove, trench, or similar structure that has been machined into the supporting bone surface. The level of security and stability that can be provided by this approach can be enhanced by various methods or devices, such as by: (i) creating a bone groove that is angled slightly toward the centerpoint of the implant, to create a "snap"-type fitting of the implant rim into the bone groove; (ii) using a swellable material, a roughened outer surface, and/or similar means to create an implant rim that will "grip" the bone groove more securely; (iii) using mechanical tightening or cinching means, shape-memory components that will shrink slightly when they warm up, or similar means to tighten the grip of the rim on the interior wall or surface of the groove or trench in the supporting bone surface; and, (iv) using other attachment means, include bone cement, which can bond to various types of polymers, and/or to other porous materials (such as wire meshes) that can be exposed on the anchoring surface of an implant.

In another preferred embodiment, a stabilizing ring can be provided with one or more segmented, protruding, or other components or surfaces (which can include eyelet devices, mesh materials, etc.) that will extend outside of the flexible polymer component of an implant. This can allow sutures, staples, bone cement, or other means to be used to secure the implant to the supporting bone.

In another preferred embodiment, a first anchoring component that does not contain a flexible polymer component can be securely affixed to a prepared bone surface, by means such as screws, staples, sutures, etc. To provide the surgeon with optimal working space, the initial anchoring steps can be performed and completed before the flexible polymer implant device is inserted into the joint that is being repaired. After that initial anchoring procedure has been completed, the flexible polymer implant can then be inserted into the joint, and either: (i) affixed directly to the first anchoring component; or, (ii) secured in place, in a manner that utilizes the anchoring component to provide greater strength and stability to the entire assembly.

Figure 6:
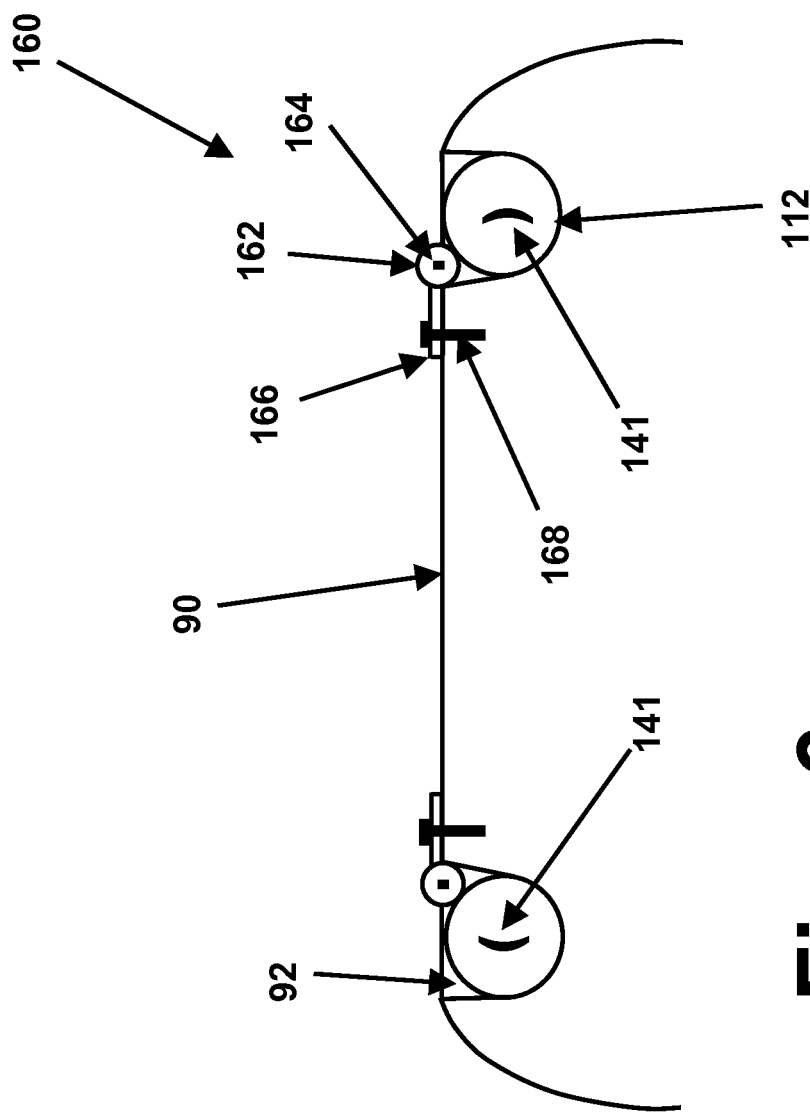
FIG. 6 is a cutaway side view depicting an anchoring component, in the shape of a large "washer" with an open center, which is securely affixed to a supporting bone by means of screws, pins, cement, etc. After that "anchoring washer" has been securely affixed to the bone, a flexible polymer implant is inserted into the joint, and the enlarged rim of the implant is pressed and nestled into a groove or trench that has been machined into the supporting bone surface. A circular ring, affixed to the anchoring washer, will cause the flexible polymer implant to "snap" into the groove or trench in the bone surface, and will thereafter prevent dislodgement of the flexible implant. For clarity.

This approach is illustrated in FIG. 6, which shows the same type of implant 100 as described above, having an enlarged rim 112 with a stabilizing ring 141 made of a shape-memory material embedded within rim 112. Stabilizing ring 141 has an arc-shaped cross-section, as described below.

After the hyaline cartilage has been removed from a bone surface 90, and after a groove 92 (sized and shaped to accommodate the rim 112 of implant 100) has been machined into the surface of the bone 90, a surgical implant that can be referred to as an "anchoring subassembly" 160 is securely affixed to the surface of bone 90, along the inner edge of the machined trench 92. Anchoring subassembly 160 comprises "trench-supplementing component" 162, which will effectively help "lock in" the enlarged rim component 112 of a flexible cartilage-replacing implant. If desired, the trench-supplementing component 162 can be provided with an internal stabilizing ring 164, made of a shape-memory, super-elastic, or similar material, embedded within the ring-shaped trench-supplementing component 162. The anchoring subassembly 160 can be securely affixed to bone 90 with the aid of an anchoring disc 166, which will be secured to the bone by a plurality of anchoring means 168 (such as screws, pins, staples, etc.). Anchoring disc 166 preferably should be provided with the shape of an enlarged washer, having an open center; accordingly, it is referred to in the claims as a "washer component". The open center will allow bone or scar tissue to grow directly into an "ingrowth surface" (as described above) on the anchoring side of the flexible polymeric implant.

The components shown in FIG. 6 are simplified, for purposes of illustration; for example, to minimize any abrasion or damage to the polymer component of an actual implant, anchoring screws or pins 168 would be countersunk into the anchoring disc 166 or into the bone surface, and the anchoring disc 166 can have a beveled, tapered, or rounded internal edge (alternately, it can be countersunk into a groove that has been machined into the supporting bone, so that the upper edge of anchoring disc 166 is flush with the prepared bone surface). In addition, while anchoring subassembly 160 as illustrated in FIG. 6 is positioned in a manner that is partially nestled into the bone trench 92, it alternately could be positioned outside the bone trench.

After the anchoring subassembly 160 has been fully anchored to the bone, a flexible polymeric implant (as shown in FIGS. 1-3) will be emplaced directly over it, and coupled to it (in FIG. 6, the flexible polymer disc that spans the center portion of the implant is not shown, to simplify the illustration of the anchoring mechanism). If desired, a "snap ring" type of securing mechanism can be used, since the tubular polymer rim 112 that surrounds the stabilizer ring 141 will be flexible. Alternately, a partially-hydrated polymer, which will swell to a larger size when fully hydrated, can be used to form the implant rim 112. If desired, bone cement or a bone-regenerating material can be used to help ensure that the implant rim 112 is firmly anchored within the groove 92 that has been machined into the surface of bone 90.

Accordingly, FIG. 6 illustrates just one of various mechanical designs that can utilize a combination of:

(i) an anchoring subassembly, which will be designed to be firmly and permanently anchored directly to a prepared bone surface, while working space is available to do so (i.e., before the flexible polymer implant is inserted into the joint, via an insertion tube); and, (ii) a flexible polymer component, which will be affixed to the anchoring subassembly in a manner which utilizes the already-affixed anchoring subassembly to provide a convenient and practical attachment mechanism that will provide a strong and stable mounting system for the flexible polymer component.

In considering the techniques and devices that are disclosed herein, it also should be noted that the anchoring means that can be used for such implants can use combinations of: (i) permanent and nonresorbable components, and (ii) resorbable sutures or other anchoring means, which can be designed to be gradually dissolved by bodily fluids while the ingrowth of bone or scar tissue into a porous anchoring surface of the implant provides permanent anchoring.

Stabilizing Rings with Variable Flexure Stiffness

In addition to the use of shape-memory materials to make the stabilizing rings disclosed herein, another design approach is disclosed herein, which utilizes controllable cross-sectional shapes to achieve (or at least facilitate) the types of behaviors and performance results that are desired for cartilage-replacing implants as disclosed herein.

This design approach can be better understood by considering the behaviors of two common household items, which are: (1) inexpensive plastic drinking straws; and, (2) metallic tape-measures.

When a standard plastic straw is bent slightly, it will exert some level of resistance, only until it reaches a point where its circular cross-section is forced to collapse. When it reaches that transition point (which can also be regarded as a failure point), it makes a rapid transition to a flattened cross-section. Once that transition occurs, the straw can be bent easily, such as into a "hairpin" shape, where the cross-sectional shape of the straw, at the apex of the curve, will be effectively flat.

A completely round and tubular straw will be damaged by that type of bending, as can be seen by the ridges, wrinkles, or other deformations that will be created where the plastic material actually bent. By contrast, a conventional metallic tape-measure (of the type that is stored in rolled-up form inside a convenient case) suffers no such damage, since its cross-sectional shape is only a shallow arc, rather than a complete circle.

Using the conventional scales that are used to describe circles, there are 360 degrees in a complete circle; an arc of 180 degrees is a half-circle; and, an arc of 90 degrees is a quarter-circle. Short metallic tape-measures (up to about 12 feet or 4 meters long) usually have arcs of about 30 to 40 degrees, while longer tape measures (up to about 25 feet or 8 meters) have arcs of about 80 degrees, to give them greater stiffness when extended out to longer lengths.

Regardless of specific dimensions, any metal tape measure is designed to remain straight, and to resist bending forces, when in use and extended, thereby allowing it to be conveniently used to measure things while someone holds the case in one hand, and uses the extended measuring tape in a manner similar to a pointing device. However, that type of stiffness is effective only until the bending force reaches a transition point, which will then force the tape to take a flattened cross-sectional shape. If a tape has been extended beyond the distance its "stiffness level" can support, it will suddenly bend somewhere along its length, and the end of the tape will fall downward. Alternately, when a measuring task has been completed and the tape must be retracted back into the case, the tape will lose its arc shape and transform into a flat layer along its entire length, as it is rolled up and retracted. Either type of transition is non-destructive; a metallic tape measure of this type will be made of a relatively elastic alloy that allows the tape measure to be extended (for use) and retracted (for storage) an unlimited number of times.

Accordingly, one preferred design for stabilizer rings as used herein can utilize an arc-shaped cross-section (similar to the cross-sectional arc of a tape measure), around at least a portion of a stabilizer ring. This design approach is illustrated in FIG. 6, in which the stabilizer ring 141 has an arc shape, which in cross-section looks comparable to a parenthesis. As long as the entire ring 141 (and indeed the entire implant 100) is in its original manufactured shape, when seen from above or below, stabilizer ring 141 will have a high or even very high degree of stiffness. That is the shape and state it will return to, and remain in, once it is nestled and settled into an accommodating groove that has been machined into a supporting bone surface. The stabilizing ring and the groove will be designed to accommodate each other, without generating any stresses or deformation on stabilizing ring 141. In that form, ring 141 can provide substantial stiffness, which is useful in a stabilizing element.

However, during the insertion step, when the entire flexible implant must be deformed in order to push it into the joint via an insertion tube, the stabilizing ring 141 can transform from its arc cross-section, into a flat cross-section that will allow almost unlimited bending, in a manner comparable to the way a metal tape-measure becomes flat at some location along its length, and thereafter allows virtually unlimited bending with virtually no resistance, once it passes a transformational (i.e., flattening and collapse) point.

Use of Twisted or Braided Cables in Stabilizing Rings and Anchoring Rims

Figure 7:
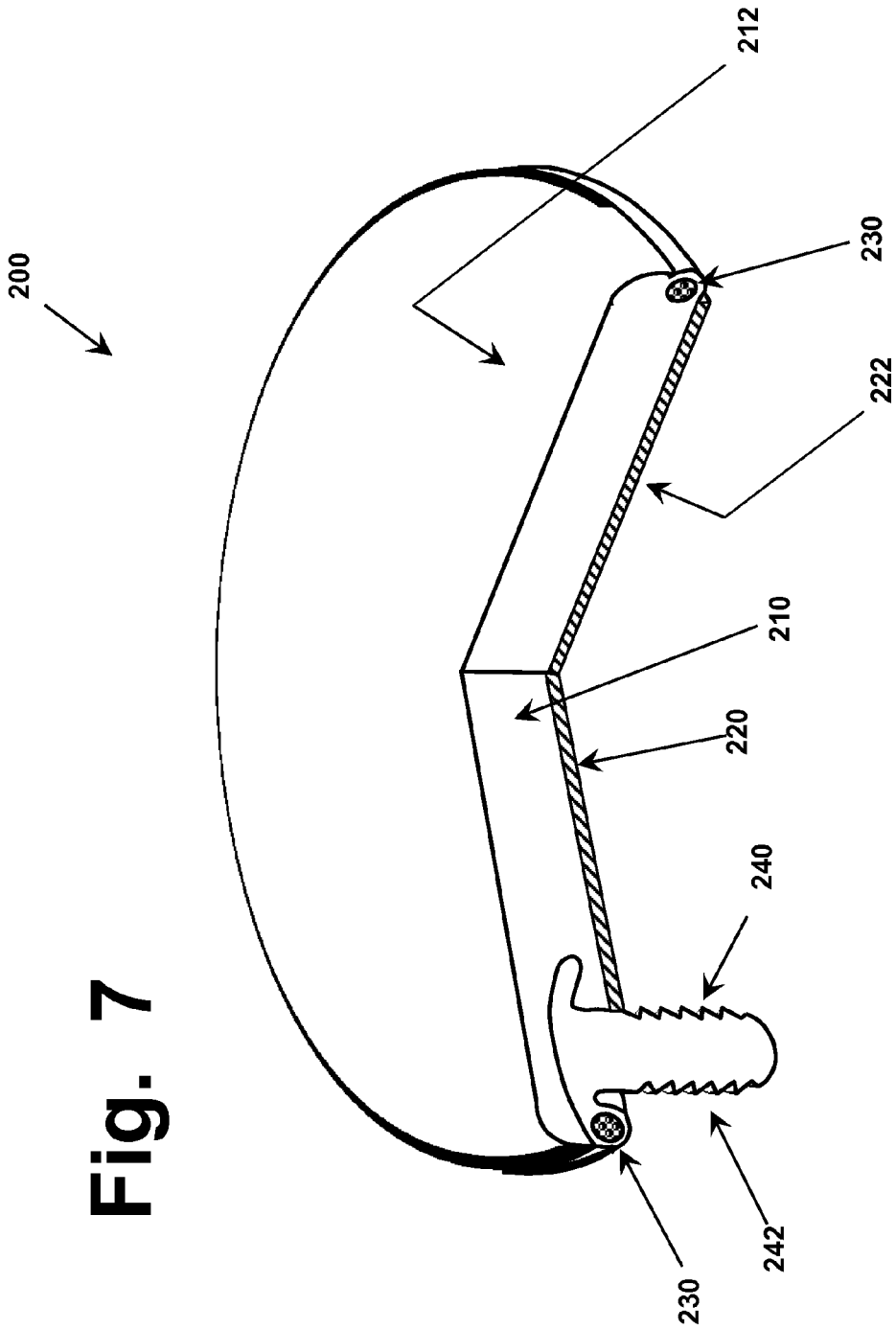
FIG. 7 is a perspective view with a partial cutaway section of a flexible implant, where the rim of the molded polymer component contains an embedded anchoring cable that is moderately stiff yet flexible. Anchoring pegs, which will engage anchoring sleeves that can be emplaced in a bone surface before the implant is inserted into a joint, are coupled to the anchoring cable at spaced locations.
Figure 8:
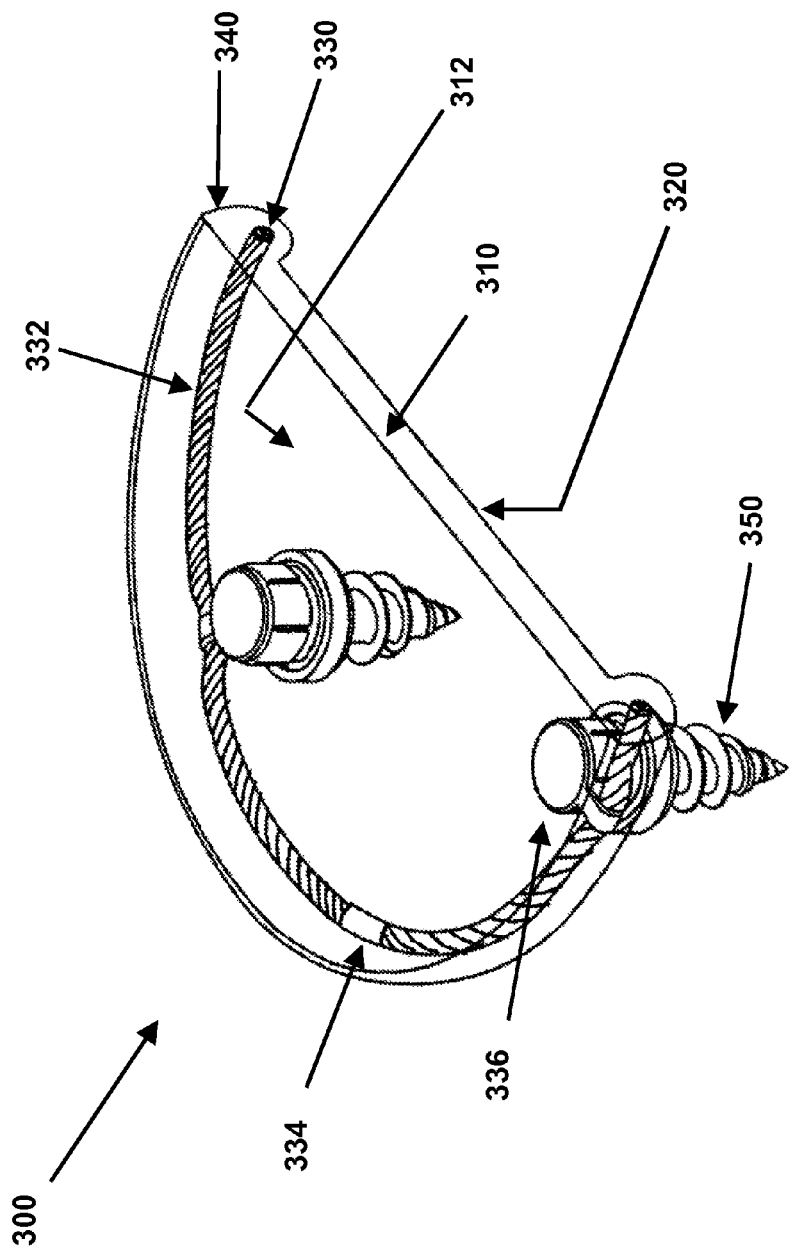
FIG. 8 is a perspective view of a cartilage-replacing implant, having a peripheral anchoring cable made of a stiff but flexible cable, embedded within a flexible polymer component that has an enlarged rim, designed to fit into an accommodating groove or trench that has been machined into the supporting bone surface. Several "snap caps" are affixed to the anchoring cable, at spaced locations. These caps will attach to the rounded heads of bone screws, which will be set in a bone surface before the implant is inserted into a joint.

As mentioned above, if desired, a stabilizing ring (as shown in FIGS. 2 and 5) or other anchoring rim component can be made of a cable, comprising twisted or braided wires or strands, as shown by cable components 230 and 330 in FIGS. 7 and 8. If this approach is used, the cable will have an irregular surface, rather than the type of completely smooth and relatively shiny surface that is found on extruded single-strand wire. This will enable a polymer that is molded around an anchoring cable to strongly and securely grip the non-smooth surface of the cable, in a manner that will prevent any slipping, sliding, or other displacement of the polymer along the length of the cable. This factor will be reflected in a higher "pullout strength", which is a testing factor that indicates the amount of tensile force required to pull a reinforcing or anchoring component out of a surrounding material.

The main components of implant 200, shown in a partial cutaway perspective view in FIG. 7, are:

(i) a flexible polymeric layer 210, which has a smooth and wettable articulating surface 212, which will replace the articulating surface of a segment of native cartilage that needs repair;

(ii) a porous layer 220, on anchoring surface 222. The anchoring surface will contact a prepared bone surface in an implant that replaces hyaline cartilage; alternately, it may contact either bone tissue or "capsular tissue" (which includes tendons, ligaments, membranes, or other soft tissues) in a meniscal implant. The porous layer will promote tissue ingrowth, for stronger and more stable long-term anchoring;

(iii) an anchoring cable 230, made of multiple moderately stiff but not rigid wires or strands 232, made of a metal alloy or suitable polymer or fiber; and, (iv) a plurality of anchoring pegs 240 that have been provided with suitable locking or affixing surfaces. In one preferred embodiment, as illustrated in FIG. 7, the locking surfaces can comprise a series of "sawtooth"-like ridges 242. Such ridges can either: (i) engage a set of corresponding ridges on the inside surfaces of anchoring sleeves, which can be emplaced in holes that have been drilled into a supporting bone surface from which damaged cartilage has been removed; or, (ii) interact with bone cement and with a drilled internal surface of a hole that has been drilled into the bone, in a manner which can eliminate a need for using anchoring sleeves embedded within a hole drilled into a bone. Alternately, if bone cement (rather than an anchoring sleeve) will be used, the ridged-type surface can be replaced by a different type of textured surface that will provide better adhesion that can be obtained with a smooth and glossy surface.

In a large implant, such as to repair a knee or hip, a plurality of anchoring pegs will be coupled to the anchoring cable 230, at suitable locations around or near the outer rim of implant 200. In a small implant, such as a "button" implant for repairing a finger or thumb joint, a single anchoring peg (or screw, as described below) can be used.

To simplify the drawing, no reinforcing mesh or other internal component is shown within polymer layer 210 of implant 200, in FIG. 2. If desired, a reinforcing mesh made of strong fibers, a non-planar perforated interface between the polymer layer and the anchoring layer, and/or any other internal component having a suitable size and shape can be embedded within the polymer layer of an implant of this type. It also should be noted that an anchoring cable is not intended or used to reinforce the polymer component of a flexible implant, in a manner that can be accomplished by means of a reinforcing mesh, a non-planar perforated interface, or other type of reinforcing component that covers all or nearly all of the "area" (when seen in a "plan" view) of the implant. Instead, the anchoring cable component 230 is intended for a different and distinct purpose, i.e., to provide the implant with a component that is located around its periphery, to provide stronger and more secure anchoring of the entire implant device, to supporting bone and/or surrounding tissue.

Implant 300, shown in FIG. 8, also has a flexible polymeric layer 310 with a smooth and wettable articulating surface 312. It normally will also have a porous layer, to promote tissue ingrowth (which leads to better long-term strength and stability) on anchoring surface 320; however, as in FIG. 2, a porous anchoring layer is not shown in FIG. 8, to simplify the illustration. Anchoring cable 330 is shown as being made of wires or strands 332, with ends that are held securely to each other by a securing collar 334, which can be crimped, soldered, welded, or otherwise securely affixed to the two ends of the cable segment, thereby establishing a continuous loop (or hoop, ring, etc.). Anchoring cable 330 is embedded within an enlarged peripheral rim 340, made of the flexible polymer material.

The primary difference between implants 200 and 300 is that, instead of using anchoring pegs that will engage sleeves that must be set into a bone surface, implant 300 uses "snap-cap" components 336, which can be "press-fit" (i.e., using compression, without requiring any rotation) onto the rounded heads of bone screws 350, which can be screwed into holes drilled into a prepared bone surface. These types of "snap-cap" attachments can use multiple "fingers" (as shown), a constrained internal "split-ring" component, or similar devices made of a non-rigid alloy that imparts spring-like behavior to a cap, to allow it to securely grip and remain affixed to a rounded or other accommodating screw head.

Figure 9:
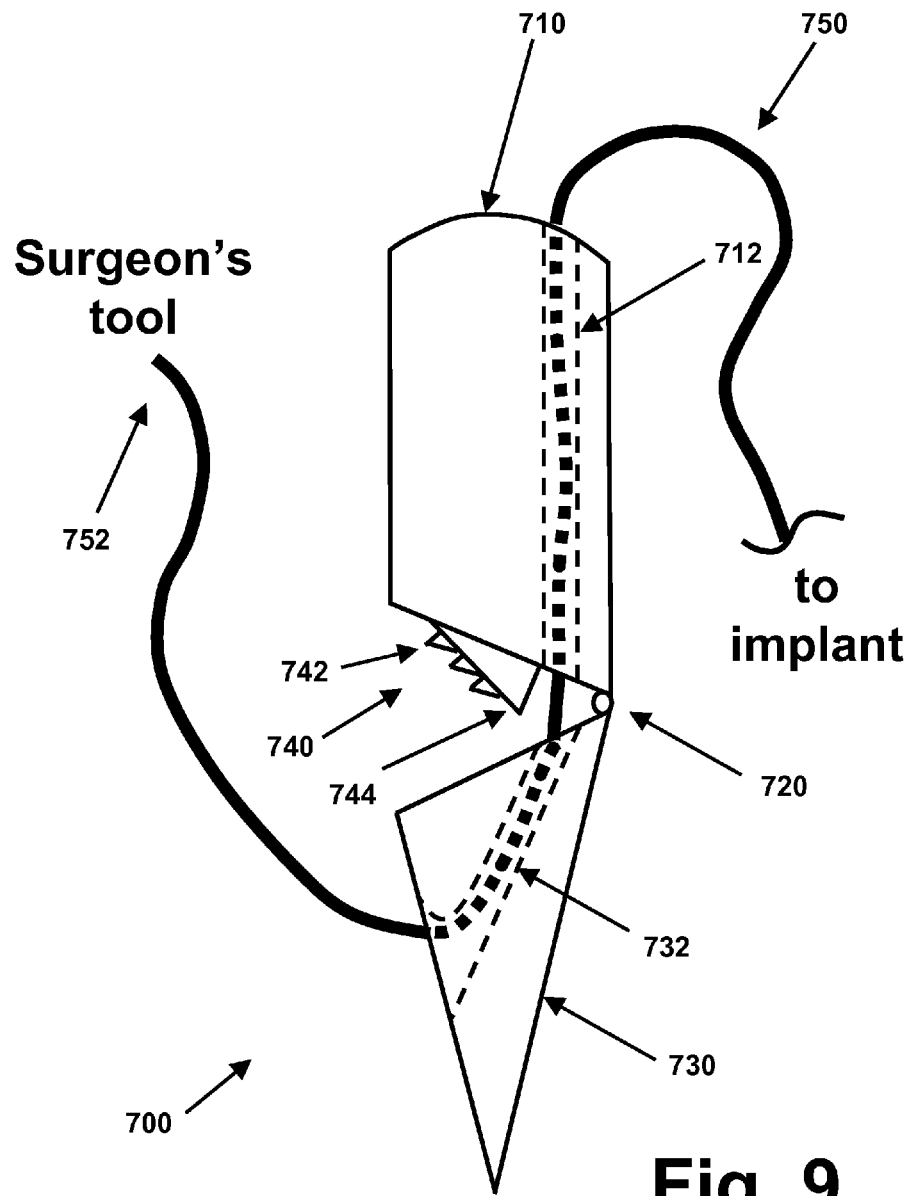
FIG. 9 depicts a type of suture anchor having a crimping mechanism which provides the suture anchor with a rachet-type control mechanism.
Figure 10:
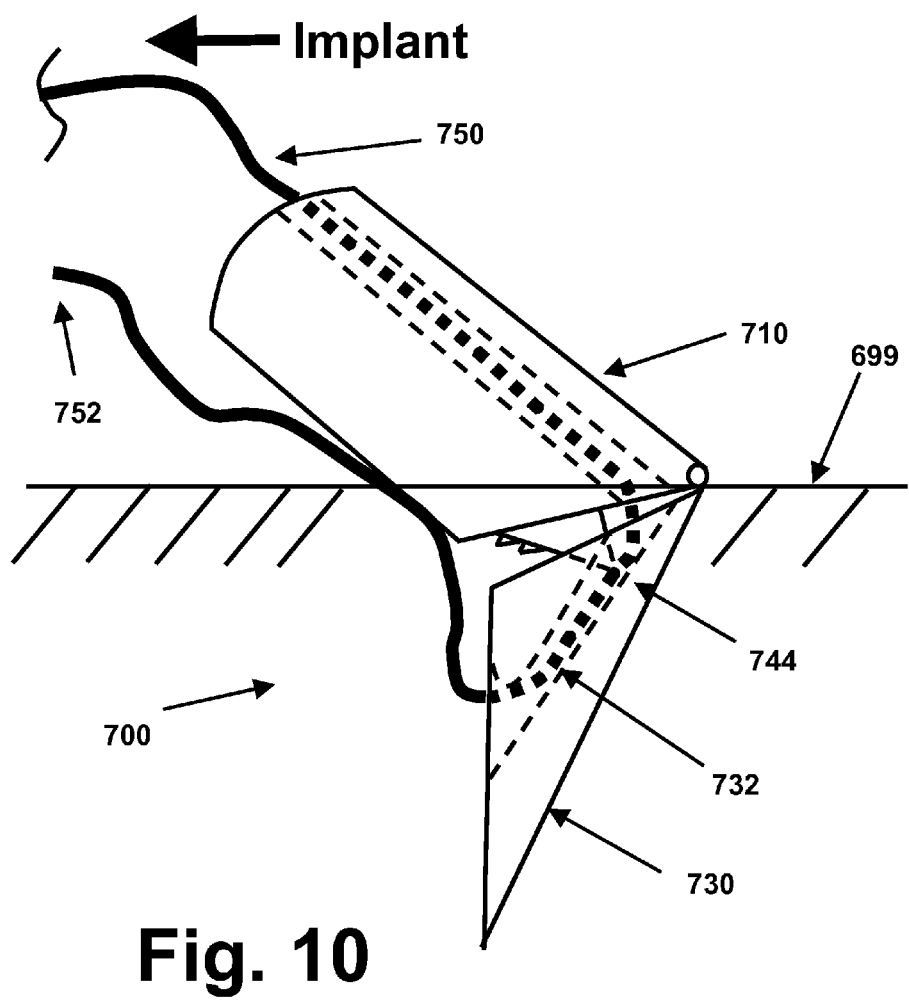
FIG. 10 depicts the same rachet-type suture anchor shown in FIG. 9, after it has been bent and crimped in a manner that prevents loosening of the suture strand which passes through the anchor.

Alternately or additionally, two other types of anchoring and securing devices that are widely used and readily available in orthopedic surgery can be adapted for use herein, to attach either or both of: (i) an anchoring cable that is embedded within the polymer component, or (ii) other components that will be used to secure the implant device, to bone or other tissue. One such class of devices is often called "fiber wires", which are cables made of twisted or braided strands of "ultra-high molecular weight polyethylene" (UHMWPE), a polymer material that has greater strength than steel cables having the same cross-sectional dimensions. The second class of devices are called "cerclage wires", which usually are made of titanium or stainless steel alloys; these commonly are used to help stabilize fractured bones, and they frequently are used with small implantable devices that allow a surgeon to "lock down" and maintain a desired level of tension on any such wire, while it is being implanted. Either of these types of cables or wires (or other comparable cables or wires) can be wrapped (preferably using several loops) around an anchoring cable as described herein, prior to pouring a prepolymerized liquid into a mold that holds the anchoring cable. A flexible implant that results from this type of manufacturing process will have several strands of high-strength wire or cable, secured to the anchoring cable within the implant, with free ends that emerging from the polymeric surface of implant. Those strands of wire or cable (which can have eyelets, loops, or other devices at their free ends) can be used by a surgeon to anchor an implant, either by themselves, or in conjunction with anchoring pegs or screws, or in conjunction with any other devices. In particular, such strands of wire or cable can pass through any of various types of "racheting anchors", which are described and illustrated in more detail in parent application Ser. No. 13/355,276, cited above. The contents of that application are incorporated herein by reference, as though fully set forth herein. In particular, that application discloses a new type of suture anchor with racheting and locking capability, which is illustrated in FIGS. 9 and 10, which are identical to FIGS. 10 and 11 in parent application Ser. No. 13/355,276.

Briefly, FIG. 9 shows racheting anchor 700 (with suture strand 750 passing through it) prior to implantation in a bone surface, while FIG. 10 shows the same racheting anchor 700 after it has been partially driven into a bone surface 699. Anchor device 700 comprises a generally cylndrical barrel portion 710, which has a tunnel or conduit 712 passing through it, and a generally conical pointed segment 730, which has a tunnel or conduit 732 passing through it. The two main segments 710 and 730 are coupled to each other by a relatively thin segment of deformable material at juncture 720, which is depicted as a circle in FIGS. 9 and 10 for purposes of illustration, since it will provide a "pivot point" comparable to a hinge. Anchoring device 700 also is provided with a "crimping ramp" 740, which has a notched, ridged, sawtooth, or other engaging surface 742, and a crimping corner or edge 744. As indicated in FIG. 10, the edge or corner 744 of crimping ramp 740 will press into and pinch the suture strand 750, in a manner which will effectively "lock down" the suture at a fixed level of tension, after the surgeon exerts a desired final level of tension on the suture strand 750 and then bends (crimps) the anchor 700.

In most cases, when an implant is used to replace hyaline cartilage (i.e., the type of thin-layer cartilage that directly covers a condylar surface of a bone), it will be anchored to a prepared bone surface from which the native cartilage has been removed (by cutting, grinding, and other steps carried out by a surgeon). This approach, using direct anchoring to a "freshened" bone surface (that term refers to a bone surface that has been scraped, abraded, or otherwise treated to force it into a "recovery mode", which will promote tissue ingrowth into the porous anchoring surface of an layer), can provide a stronger, more stable, and more durable anchoring attachment, compared to laying an implant on top of diseased or injured cartilage that has not been removed from a bone condyle.

As briefly mentioned above, if an anchoring cable 230 or 330 is made of a cable comprising twisted or braided wires or strands, it will have an irregular surface, rather than the type of completely smooth and relatively shiny surface that is found on single-strand wire of the type that is created by an extrusion process. This will enable a polymer that is molded around an twisted or braided cable to strongly and securely grip the non-smooth surface of the cable, in a manner that will prevent any slipping, sliding, or other displacement of the polymer along the length of the cable. This factor will be reflected in a higher "pullout strength", which is a testing factor that indicates the amount of tensile force required to pull a reinforcing or anchoring component out of a surrounding material.

If a cable is used to provide a stabilizing ring or anchoring rim, it should have a proper balance between stiffness, and flexibility (also referred to by terms such as pliability). A complete implant assembly (which will include an anchoring cable embedded within a flexible polymer component) must be sufficiently pliable and flexible to allow it to be rolled up into a cylindrical configuration that can pass through an arthroscopic insertion tube, during a surgical implantation procedure. There is no fixed size limit for arthroscopic insertion tubes; nevertheless, the pressing and overriding goal of any such operation is to minimize the diameter of a tube that must be passed through the tissue that surrounds a joint, in order to minimize the damage that must be inflicted on any tendons, ligaments, muscles, blood vessels, or other soft tissues in the region that is being repaired. Accordingly, if a cable-anchored polymer implant has sufficient flexibility to allow it to be inserted into a joint via the smallest "practical" insertion tube, that flexibility can minimize: (i) the damage that must be inflicted on surrounding tissues during surgery; (ii) the pain and recovery time that must be endured by the patient; (iii) the risk of infection, which will remain a threat until any incisions have fully closed and healed; and, (iv) the risk of creating a lasting unwanted post-repair condition what has been rendered suboptimal by unwanted scar tissue, improper tissue regeneration, infection, or similar factors.

However, after surgical insertion has been completed, a moderately stiff anchoring cable can help secure and stabilize an implant that will replace a segment of hyaline cartilage that directly covers a hard bone surface. This arises from the fact that an enlarged implant rim (such as rim 240, shown in FIG. 2) can be fitted and nestled into an accommodating groove or trench that can be machined (with the aid of templates, computer-guided cutting tools, or similar devices) into a hard bone surface. If a jarring-type impact is caused by a jump, fall, accident, etc., or if a low level of stress in the implant or the supporting bone is created by a non-optimal installation, any resulting stresses will be distributed and "smoothed out" over larger areas of both the bone and the implant, leading to higher levels of strength, durability, and resistance to wear, degradation, or damage.

By contrast, if a meniscal implant (or any other implant) is designed to be affixed to tendons, ligaments, or other non-bone tissue, the anchoring cable generally should not be provided with high levels of stiffness, and instead should be able to emulate and accommodate the flexibility of the surrounding soft tissue. In this type of arrangement, an anchoring cable made of thin and flexible fibers of a biocompatible polymer with high tensile strength is likely to be preferable to a cable made of titanium or other metal alloy. In such a case, the function of the cable effectively will be to distribute and allocate any "point-loaded" stresses around a much larger area of the implant, thereby converting any localized "peak loadings" that might cause unacceptably high stresses, into low-level distributed stresses that will not cause any damage, even over a span of decades.

The proper balance between flexibility and stiffness, in an anchoring cable, will depend on the size, shape, and insertion site of an implant. As a simple illustration, an implant designed to replace a femoral runner, in a knee, will have very different traits compared to an implant designed to repair a finger joint. To provide anchoring cables that can be positioned at any location along a very wide spectrum, with "extremely flexible" at one end and "extremely stiff" at the other end of the spectrum, three physical parameters can be modified and controlled, for any starting material, such as a titanium alloy or a suitable polymer. Those three physical traits are:

1. the thickness of each strand, which can range anywhere from (i) thin and fine wires (with diameters less than 0.1 mm) that can be readily bent, to (ii) thick and heavy wires (with diameters greater than 1 mm) that, when aggregated into a cable, can be bent only with the use of tools;

2. the number of strands that will be incorporated into a cable, which in most cases will range between 3 (for relatively thick strands) and about 20 (for relatively thin strands); and, 3. the looseness or tightness of the twisting or braiding structure, in a cable. If a cable with a twisted helical structure made of wire strands is wrapped tightly (such as with several helical turns per centimeter of cable length), it will be stiffer than a cable that is wrapped loosely, within only a single turn (or a fraction of a turn) per centimeter of length.

By controlling those dimensional traits, a cable that is manufactured from a particular type of suitable alloy or polymer can be given any desired level of stiffness. Furthermore, a cable can be manufactured from an assortment of strands having different diameters, and/or made of different materials. For example, a cable made with one, two, or three strands of a relatively stiff metal alloy (such as stainless steel) having one or more chosen diameters, combined with a number of very thin strands of a polymer having high tensile strength but low stiffness (such as conventional nylon fibers), can be created with any desired level of stiffness.

Accordingly, a manufacturer can use these directly-controllable options and parameters to create an anchoring cable (either in a continuous loop, or in segments) that balances flexibility against stiffness at a level that is optimized for any type of implant having a known size, shape, and intended site of implantation.

Flexible Cables for Anchoring Meniscal Implants

Figure 11:
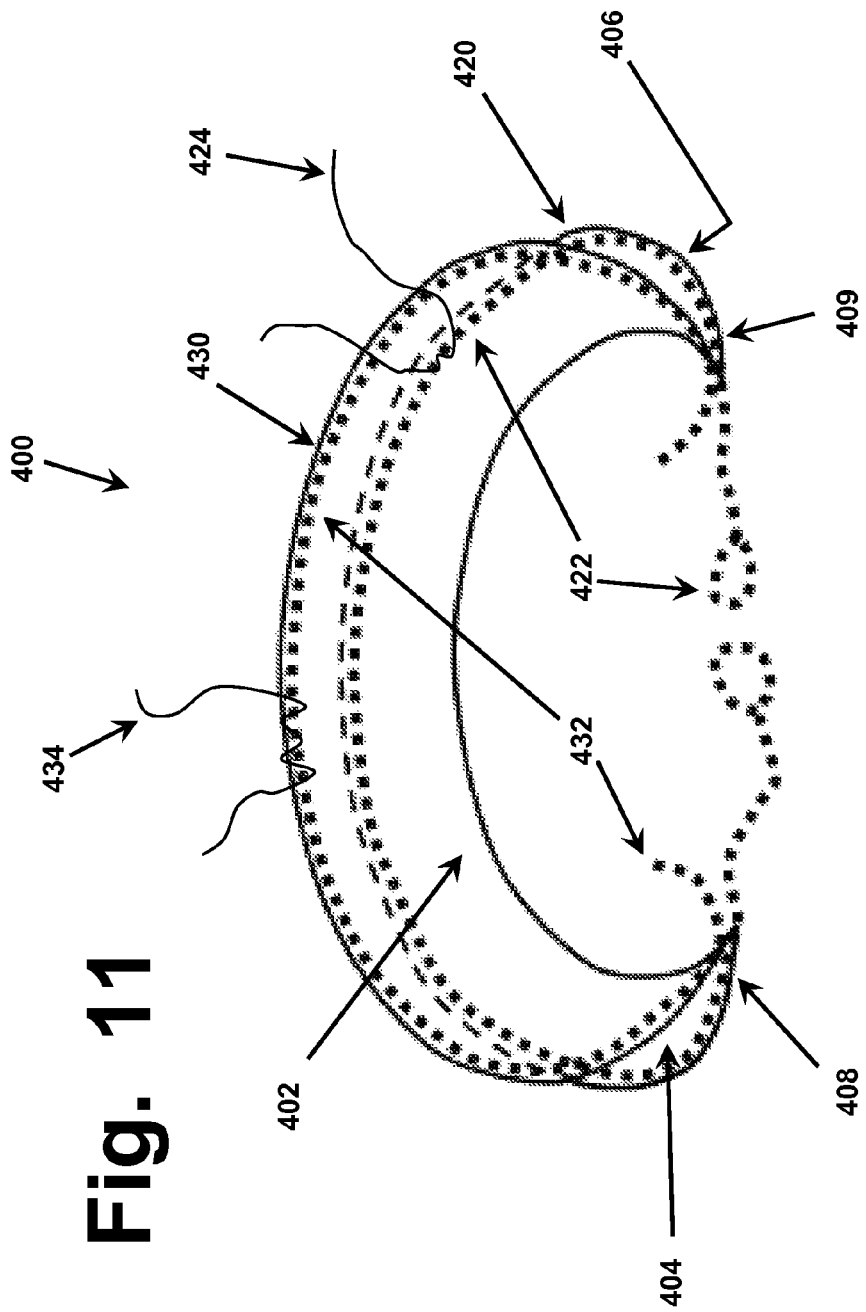
FIG. 11 is a cutaway view, showing upper and lower flexible anchoring cables embedded within a polymer segment having the size and shape of a meniscal wedge. A suture strand is shown wrapped around one cable, with both ends of the suture strand emerging from the polymer segment; this allows the ends of the suture strand to be used to anchor the peripheral surface of the meniscal implant, to the soft tissues that form the knee capsule. The ends of the anchoring cables are designed to be affixed to the tibial plateau, in a manner and location that emulates the anchoring of natural meniscal segments.

FIG. 11 depicts a meniscal implant 400, which has a shape that can be referred to as an arc-shaped (or "arcuate") wedge, somewhat similar to a section from a tangerine or other citrus fruit. Regardless of whether a native meniscal segment is on the interior or lateral side of a knee joint, it will have three important surfaces, indicated in FIG. 9 as:

(i) an upper articulating surface 402, which will be smooth and "lubricious", and which will press and articulate against the rounded bottom surface of a femoral runner (ii) an outer peripheral surface 404, generally in the shape of a vertical cylindrical segment, which will not articulate against cartilage, and which instead will be coupled to the tissues which form a "knee capsule" (i.e., the tendons, ligaments, and membranes which enclose and hold in the synovial fluid, which lubricates a knee joint); and, (iii) a smooth and lubricious lower surface 406, which is roughly planar, and which rests upon and slides against an upper surface of a tibial plateau. This lower surface is bounded and defined by a first arcuate interior edge, a second arcuate peripheral edge, and opposing tips 408 and 409 where said first and second arcuate edges meet.

Accordingly, in one preferred embodiment, meniscal implant 400 is anchored, stabilized, and reinforced with the aid of two different elongated flexible reinforcing members, which are depicted by "beaded lines" 422 and 432 in FIG. 9. Reinforcing member 422 is positioned along or near the "lower" outer peripheral edge 420 of the meniscal wedge 400, and reinforcing member 432 is positioned along or near the "upper" outer peripheral edge 430 of the meniscal wedge 400.

For similicity of illistration, both of the reinforcing members 422 (lower) and 432 (upper) are depicted as extending out of and beyond the two opposing tips 408 and 409 of the flexible polymer material. In actual practice, either or both of the lower and upper reinforcing members 422 and 432 are likely to be coupled, at each end, to a plug-type device that is coupled directly to (or positioned closely adjacent to) the two tips 408 and 409 of the meniscal wedge. These types of plug-type anchoring components can be set into small holes that have been drilled into a tibial plateau, in a manner that provides a larger, more distributed, and therefore stronger anchoring interface than can be achieved by a single screw or pin.

In addition, it likely will not be essential, in all cases, to provide two different reinforcing members along both the lower and upper peripheral edges of a meniscus. For example, if the entire polymer component is reinforced by a fiber mesh, that mesh can eliminate the need for a second elongated reinforcing member along the upper peripheral edge of the meniscal wedge.

Thus, there has been shown and described a new and useful design for surgical implants for replacing and repairing cartilage. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

The invention claimed is:

1. A surgical implant assembly, configured for affixing a hyaline cartilage replacement implant on a bone surface adjacent to a machined rounded groove with an edge formed in a bone of a knee joint, the implant assembly comprising:

a flexible hyaline cartilage replacement implant having a smooth lubricious articulating surface on an exposed side and an enlarged rounded rim protruding on a side opposite from the exposed side, wherein the enlarged rim is dimensioned and adapted to fit into the groove for affixing the flexible cartilage replacement implant in place on the surface; and an anchoring subassembly, said anchoring subassembly comprising:

an anchoring washer component with an open center area, the washer component comprising anchoring screws or pins and configured for permanent attachment to the bone surface such that an edge of the washer component extends along an edge of the groove; and a ring-shaped trench supplementing component affixed to the washer component, the trench supplementing component dimensioned for extending beyond edge of the groove;

wherein the trench supplementing component and the enlarged rim are dimensioned such that the enlarged rim is snapped resiliently over the trench supplementing component in order to be fit into the groove, whereby the enlarged rim becomes locked in the groove, wherein the machined groove extends around a periphery of the bone surface, wherein the washer component is disposed within said periphery and the trench supplementing component extends outwardly from the washer component, and wherein the enlarged rim of the implant snaps resiliently over the trench supplementing component into the groove.

2. The surgical implant assembly of claim 1, wherein the enlarged rim is configured to shrink after insertion.

3. The surgical implant assembly of claim 1, wherein the trench supplementing component and the enlarged rim are cross sectionally shaped to lock the enlarged rim in the groove.

4. The surgical implant assembly of claim 1, wherein said anchoring screws or pins are configured for extending through the washer component and into the bone surface.

5. The surgical implant assembly of claim 1, further comprising a flexible elongated reinforcing member embedded in the enlarged rim.

* * * * *